US012589200B2

(12) United States Patent
    Boddington

(10) Patent No.: US 12,589,200 B2
(45) Date of Patent: Mar. 31, 2026

(54) FLUIDIC SIGNAL CONTROL DEVICE

(71) Applicant: i:Med (Europe) Ltd., Byfield (GB)

(72) Inventor: Tim Boddington, Byfield (GB)

(73) Assignee: i:Med (Europe) Ltd.

( * ) Notice: Subject to any disclaimer, the term of this patent is extended or adjusted under 35 U.S.C. 154(b) by 990 days.

(21) Appl. No.: 17/776,995

(22) PCT Filed: Nov. 12, 2020

(86) PCT No.: PCT/GB2020/052875
    § 371 (c)(1),
    (2) Date: May 13, 2022

(87) PCT Pub. No.: WO2021/094754
    PCT Pub. Date: May 20, 2021

(65) Prior Publication Data
    US 2022/0379007 A1      Dec. 1, 2022

(30) Foreign Application Priority Data

Nov. 15, 2019    (GB) ..................................... 1916684

(51) Int. Cl.
    *A61M 5/00*          (2006.01)
    *A61M 5/145*         (2006.01)
(52) U.S. Cl.
    CPC ... *A61M 5/007* (2013.01); *A61M 2005/14513* (2013.01); *A61M 2205/071* (2013.01); *A61M 2209/01* (2013.01)
(58) Field of Classification Search
    CPC ........ A61M 5/007; A61M 2005/14513; A61M 2205/071; A61M 2209/01; A61B 6/481
    (Continued)

(56) References Cited

U.S. PATENT DOCUMENTS

| 4,169,353 | A | | 10/1979 | Fresard | |
| 5,515,851 | A | * | 5/1996 | Goldstein | ........... A61M 3/0233 |
| | | | | | 600/431 |

(Continued)

FOREIGN PATENT DOCUMENTS

| CN | 103961765 | A | * | 8/2014 | ........ A61M 5/14248 |
| EP | 1653493 | | | 5/2006 | |

(Continued)

OTHER PUBLICATIONS

International Search Report and Written Opinion dated Feb. 9, 2021 in Application No. PCT/GB2020/052875.

(Continued)

*Primary Examiner* — Brian L Casler
(74) *Attorney, Agent, or Firm* — Snell & Wilmer L.L.P.

(57) ABSTRACT

There is provided a control device for providing a fluidic signal to a medical infusion apparatus, the device comprising a housing and a pressure control sheet, wherein the pressure control sheet is formed from a deformable and resilient material, and the pressure control sheet is secured to and forms a seal with the housing such that the housing and the pressure control sheet together define a first chamber and an independent second chamber, wherein the pressure control sheet is arranged so that the fluid pressure within each chamber can be changed upon input from a user. The control device further comprises a first fluid conduit member in fluid-flow communication with the first chamber and a second fluid conduit member in fluid-flow communication with the second chamber, wherein, in use, inputs from a user change the fluid pressure within the chambers which causes movement of fluid through the fluid conduit members to provide fluidic signals.

12 Claims, 8 Drawing Sheets

(58) Field of Classification Search
  USPC ..................................................... 600/431, 5
  See application file for complete search history.

(56)       References Cited

U.S. PATENT DOCUMENTS

| | | |
|---|---|---|
| D404,717 S | 1/1999 | Duchon et al. |
| 5,881,917 A | 3/1999 | Jones et al. |
| 5,916,165 A | 6/1999 | Duchon et al. |
| D618,334 S | 6/2010 | Le et al. |
| 2009/0208385 A1 | 8/2009 | Howorth et al. |

FOREIGN PATENT DOCUMENTS

| | | |
|---|---|---|
| FR | 2463303 | 2/1981 |
| WO | 2001075918 | 10/2001 |
| WO | 2011091075 | 1/2011 |

OTHER PUBLICATIONS

Search Report dated May 14, 2020 in Great Britain Patent Application No. GB1916684.2.

* cited by examiner

FLUIDIC SIGNAL CONTROL DEVICE

CROSS-REFERENCE TO RELATED APPLICATIONS

This application is a U.S. national stage entry under 35 U.S.C. § 371 of International Application No. PCT/GB2020/052875 filed Nov. 12, 2020, entitled "FLUIDIC SIGNAL CONTROL DEVICE," which claims priority to, and the benefit of, Great Britain Patent Application Serial No. 1916684.2, filed on Nov. 15, 2019. Each of the foregoing applications are hereby incorporated by reference in their entirety (except for any subject matter disclaimers or disavowals, and except to the extent of any conflict with the disclosure of the present application, in which case the disclosure of the present application shall control).

FIELD OF THE INVENTION

The invention relates to an improved control device for providing a fluidic signal to a medical infusion apparatus. The invention utilises a pressure control sheet system and avoids the use of air bladders to provide a reliable and safe medical device for reduced risk to patient safety.

BACKGROUND TO THE INVENTION

Angiography is a procedure used in the detection and treatment of abnormalities or restrictions in blood flow within the coronary arteries. During angiography, a fluoroscopy image of a vascular structure is obtained by injecting radiographic contrast media through a catheter into an artery. The vascular structures are fluidly connected with the artery in which the injection occurred and are filled with contrast media. X-rays are passed through the region of the body in which the contrast media was injected. The X-rays are absorbed by the contrast media, causing a radiographic outline or image of the blood vessel containing the contrast media. The X-ray images of the blood vessels, filled with the contrast media, are usually recorded onto photographic film or a special detector and are displayed on a fluoroscope monitor. A further interventional procedure may be performed as an extension of the angiography, which involves the placement of a balloon catheter or stent. This is introduced into the blocked or diseased artery. This is known as percutaneous coronary intervention (PCI) or angioplasty.

During angiography, a physician places a series of catheters into the coronary arteries and the angiographic catheters are routinely connected to a monitoring device such as an ACIST CVi® injector. Fluid flow is controlled by use of a remote hand controller. The remote hand controller has one button to inject contrast media and one button to inject saline. Saline is used to remove air from the system because it is isotonic with blood. The removal of air from the system is crucial as air in the bloodstream may cause embolism, stroke or death. The user of the remote hand controller adjusts the rate and volume of injection of contrast media or saline by altering the manual actuation force applied to the corresponding buttons of the remote hand controller. The manual actuation force drives a column of air into a sensor in the monitoring device which then transmits a signal to one of two pumps. The pumps regulate the flow of contrast media or saline through the disposable lines of the ACIST CVi® injector and into the heart.

U.S. Pat. No. 5,916,165 describes a pneumatic control device which functions as a remote hand controller. The device includes a housing, a pressure control member secured to the housing, a first fluid conduit member and a first sensor. The pressure control member is constructed and arranged to selectively change a fluid pressure within the control member. In some systems, the pressure control member includes a first air bladder oriented within the housing interior and comprising a resilient material.

Improvements to existing systems are sought to improve performance and reduce risks to patient and staff safety.

SUMMARY OF THE INVENTION

The present invention relates to a control device for providing a fluidic signal to a medical infusion apparatus. This fluidic signal can be provided to a machine, for example, to a contrast delivery machine for angiography such as the ACIST CVi® machine. The present invention is a significant improvement over the prior art as it utilises a pressure control sheet system rather than an air bladder system. The present invention prevents fluid leakage from the system and reduces the risk to patient safety. The design also allows for simpler and cheaper manufacture.

The present invention provides a control device for providing a fluidic signal. The device comprises a housing, a pressure control sheet and a first and a second fluid conduit member. The pressure control sheet is formed from a deformable and resilient material and is secured to and forms a seal with the housing such that the housing and the pressure control sheet together define a first and a second chamber. The second chamber is independent of the first chamber. The pressure control sheet is arranged so that the fluid pressure within the chamber can be changed upon input from a user. The first fluid conduit member is in fluid-flow communication with the first chamber. The second fluid conduit member is in fluid-flow communication with the second chamber. In use, a first input from a user changes the fluid pressure within the first chamber which causes movement of fluid through the first fluid conduit member to provide a first fluidic signal. A second input from a user changes the fluid pressure within the second chamber which causes movement of fluid through the second fluid conduit member to provide a second fluidic signal.

The pressure control sheet may be formed from any suitable deformable and resilient material. This has the benefit that the pressure control sheet can be deformed to selectively change the fluid pressure in the first or second chamber in order to generate a first or second fluidic signal. The pressure control sheet may be formed from a plastic, preferably a thermoplastic elastomer. The pressure control sheet may be formed from a thermoplastic urethane (TPU), thermoplastic elastomer (TPE), silicone, polyethylene or polyvinyl chloride (PVC). The pressure control sheet may be formed from a material comprising a plasticizer. Preferably, the pressure control sheet is formed from plastic. More preferably, the pressure control sheet is formed from medical grade plastic. This has the advantage that the device is safe for the patient and can be sterilised. More preferably, the pressure control sheet is formed from medical grade phthalate-free plastic. For example, the pressure control sheet may be formed from plastic comprising Dioctyl terephthalate (bis(2-ethylhexyl) benzene-1,4-dicarboxylate; (DEHT). DEHT-comprising plastics have the advantage that they are less liable to create a carcinogenic risk and are safer for the patient, compared to phthalate-comprising plastics, such as di(2-ethylhexyl)phthalate (DEHP). Preferably, the pressure control sheet is formed from PVC comprising DEHT.

The chambers may have any volume. Preferably, the first chamber has a volume selectively adjustable to change the fluid pressure within the first chamber and cause movement of fluid through the first fluid conduit member. Preferably, the second chamber has a volume selectively adjustable to change the fluid pressure within the second chamber and cause movement of fluid through the second fluid conduit member.

The pressure control sheet may be secured to the housing by any securing means. The pressure control sheet may be secured to the housing by crimping, welding, soldering, brazing, taping, gluing or the use of other adhesives, magnetism, suction and/or friction. Preferably, the pressure control sheet is secured to the housing by crimping. The pressure control sheet may be contacted on its upper and lower surface by the housing to secure the pressure control sheet to the housing. The pressure control sheet may have a plurality of holes through which it is secured to the housing. The pressure control sheet may have any number of holes, preferably 2-10 holes, more preferably 4-8 holes, even more preferably 6 holes.

The securing means form a seal between the pressure control sheet and the housing. The seal may be achieved by adhesion, or preferably by compression. The pressure control sheet may be in direct contact with the housing to create the seal, or may be indirectly contacting the housing to create a seal (for example, via an O-ring). The chambers may be sealed by the seal.

The pressure control sheet is secured to the housing such that the housing and the pressure control sheet together define a first chamber and a second chamber. Preferably, the first chamber is sealed except for the fluid-flow communication with the first fluid conduit member, and the second chamber is sealed except for the fluid-flow communication with the second fluid conduit member. This means that any change in pressure in the first chamber is transmitted to the first fluidic conduit member and causes movement of fluid through the first fluid conduit member, and any change in pressure in the second chamber is transmitted to the second fluidic conduit member and causes movement of fluid through the second fluid conduit member.

The pressure control sheet may be formed from a unitary length of material. This has the advantages of reduced risk of fluid leakage (especially air leakage) and simpler manufacture. Furthermore, the air bladder systems of the prior art require each air bladder to be oriented in an exact manner within the housing interior. This invention obviates this requirement, ensuring faster and more reliable manufacture.

The pressure control sheet may have at least two projections, where the projections and the housing define the chambers. The projections may be any shape. The projections may be button-shaped. Preferably, the projections are substantially hemispherical or substantially cylindrical.

The housing may be formed from any suitable material. Preferably, the housing is formed from a non-deformable material. Preferably, the housing is formed from an inexpensive, lightweight material. Preferably, the housing is formed from a material that can be sterilised. Preferably, the housing is formed from a medical-grade material. The housing may be formed from a plastic, preferably from a thermoplastic, and more preferably from PVC, polycarbonate, nylon, or acrylonitrile butadiene styrene (ABS). The housing may be smooth or textured. Preferably, the housing is textured to aid gripping of the control device with wet and/or gloved hands. Any method known by one skilled in the art to create texture in a surface of a material may be used. Texture may be formed during the moulding process, for example by forming indentations or grooves in the material. Preferably, the housing is sized to comfortably fit within a user's hand.

The housing may define a wall that encloses a housing interior. At least a portion of the pressure control sheet may be positioned within the housing interior. The wall may define at least two apertures. The apertures may provide access to the pressure control sheet. The apertures may be any shape. At least a portion of the pressure control sheet may be positioned outside the housing interior. At least a portion of the pressure control sheet may extend through the at least two apertures, such that the pressure control sheet may be controlled by the user. Preferably, the at least two projections each extend through an aperture. The projections and the apertures may have substantially the same diameter.

In particular embodiments the fluid of the control device is a gas. The gas may be any suitable gas, for example, it may be air, nitrogen, etc. In some embodiments, the fluid is air.

The first input from the user may be a compression of the pressure control sheet. The time period of the input may vary. Compression of the pressure control sheet may cause fluid to flow through the first fluid conduit member. In particular, compression of the pressure control sheet may create positive air pressure within the first chamber, causing an air column to flow through the first fluid conduit member.

The first fluid conduit member is in fluid-flow communication with the first chamber which is formed by the housing and the pressure control sheet together. Preferably, the first fluid conduit member is connected to the housing so that a change in the fluid pressure within the first chamber causes movement of fluid out of an aperture in the housing and into the first fluid conduit member.

The first fluid conduit member may comprise a flexible lumen. The first fluid conduit member may be formed from any suitable material. Preferably, the first fluid conduit member is formed from a material that can be sterilised. Preferably, the first fluid conduit member is formed from a medical-grade material. The first fluid conduit member may be formed from a plastic, preferably from a thermoplastic, and more preferably from a phthalate-free thermoplastic. For example, the first fluid conduit member may be formed from PVC comprising DEHT.

The first fluid conduit member may comprise attachment means to allow it to be connected to a machine, for example, to a contrast delivery machine for angiography and/or PCI such as the ACIST CVi® machine. The attachment means may be any suitable attachment means including a luer lock.

When attached to a machine, for example, to a contrast delivery machine for angiography and/or PCI (such as the ACIST CVi® machine), the control device may be connected to a first sensor so that the first fluid conduit member is in fluid-flow communication with the first sensor. This means that when fluid moves through the first fluid conduit member to provide a first fluidic signal, this movement/signal can be detected by the first sensor. The first sensor may be constructed and arranged to generate a first control signal based upon the fluid pressure within the first chamber via movement of fluid through the first fluid conduit member.

In a preferred embodiment, the control device includes a pressure control sheet having a first projection and a second projection, said projections and the housing defining the first chamber and the second chamber. The first and second chambers are fluidly independent from one another. The projections may be formed in the same surface of the pressure control sheet. Preferably, the wall defines a first aperture and a second aperture. The first and second aper-tures may be in the same plane. The first and second apertures may be in parallel planes. In one aspect, the first aperture is in a first plane, the second aperture is in a second plane; and the first and second planes intersect at an oblique angle. In another aspect, the first aperture is in a first plane, the second aperture is in a second plane; and, the second plane is normal to the first plane. Preferably, a first projec-tion extends through a first aperture and a second projection extends through a second aperture. Preferably, the first projection is substantially hemispherical and the second projection is substantially cylindrical projection. This has the advantage that the projections feel distinct to the user, reducing the risk of injecting the wrong fluid into the patient.

The control device includes a second fluid conduit mem-ber in fluid-flow communication with the second chamber, wherein, in use, a second input from a user changes the fluid pressure in the second chamber which causes movement of fluid through the second fluid conduit member to provide a second fluidic signal.

The second input from the user may be a compression of the pressure control sheet. The time period of the second input may vary. Compression of the pressure control sheet may cause fluid to flow through the second fluid conduit member. In particular, compression of the pressure control sheet may create positive air pressure within the second chamber, causing an air column to flow through the second fluid conduit member.

The second fluid conduit member may comprise a flexible lumen. The second fluid conduit member may be formed from any suitable material. Preferably, the second fluid conduit member is formed from a material that can be sterilised. Preferably, the second fluid conduit member is formed from a medical-grade material. The second fluid conduit member may be formed from a plastic, preferably from a thermoplastic, and more preferably from a phthalate-free thermoplastic. For example, the second fluid conduit member may be formed from PVC comprising DEHT. In some aspects, the first and second fluid conduit members are formed from the same material as a twin tubing element.

The second fluid conduit member may comprise attach-ment means to allow it to be connected to a machine, for example, to a contrast delivery machine for angiography and/or PCI such as the ACIST CVi® machine. The attach-ment means may be any suitable attachment means includ-ing a luer lock.

When attached to a machine, for example, to a contrast delivery machine for angiography and/or PCI (such as the ACIST CVi® machine), the control device may be con-nected to a second sensor so that the second fluid conduit member is in fluid-flow communication with the second sensor. This means that when fluid moves through the second fluid conduit member to provide a second fluidic signal, this movement/signal can be detected by the second sensor. The second sensor may be constructed and arranged to generate a second control signal based upon the fluid pressure within the second chamber via movement of fluid through the second fluid conduit member.

In a preferred embodiment, the first chamber controls dispersal of contrast media to a patient and the second chamber controls dispersal of saline fluid to a patient.

BRIEF DESCRIPTION OF THE DRAWINGS

The invention will now be described in detail by way of example only with reference to the figures in which.

DETAILED DESCRIPTION OF THE INVENTION

Figure 1:
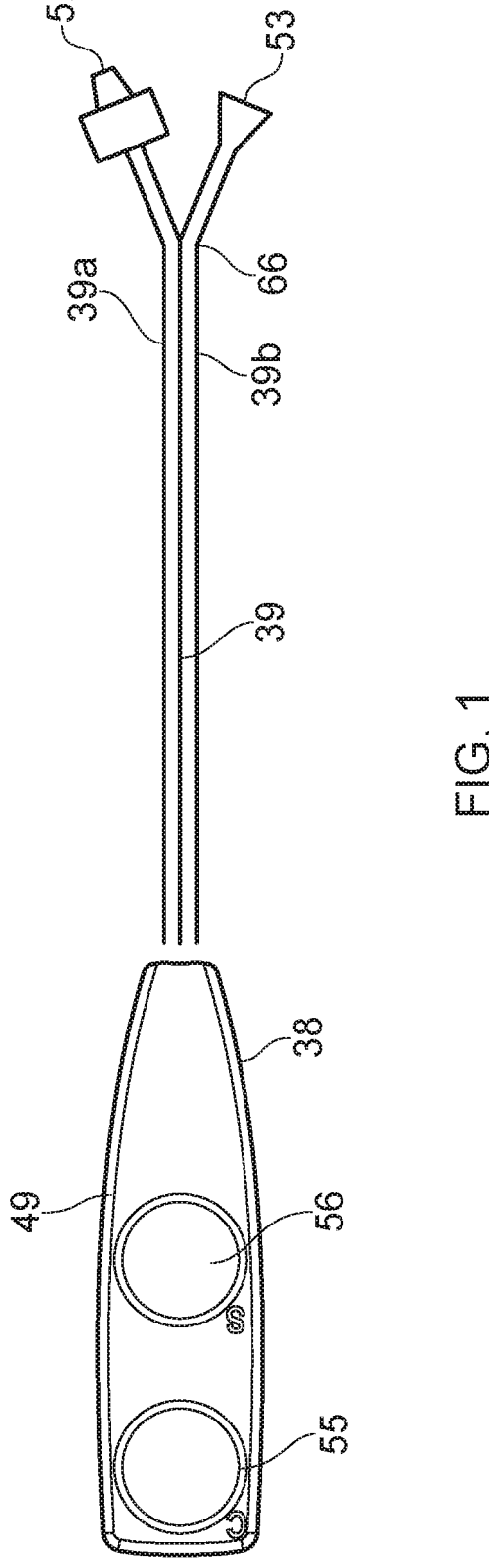
FIG. 1 shows the device with key components. Two projections (55, 56) protrude through apertures in the bottom housing (38) to form two chambers. The chambers are operably connected to two fluid conduit lines (39a, 39b) formed as twin tubing (39). The fluid conduit lines (39a, 39b) are connected to Luer Lock connectors (52, 53) to allow the tubing to be connected to the machine. The twin tubing (39) is bifurcated inside the housing to allow con-nection to the individual chambers, and at a point (66) to allow connection of the Luer Lock connectors to separate ports on the machine.
Figure 2:
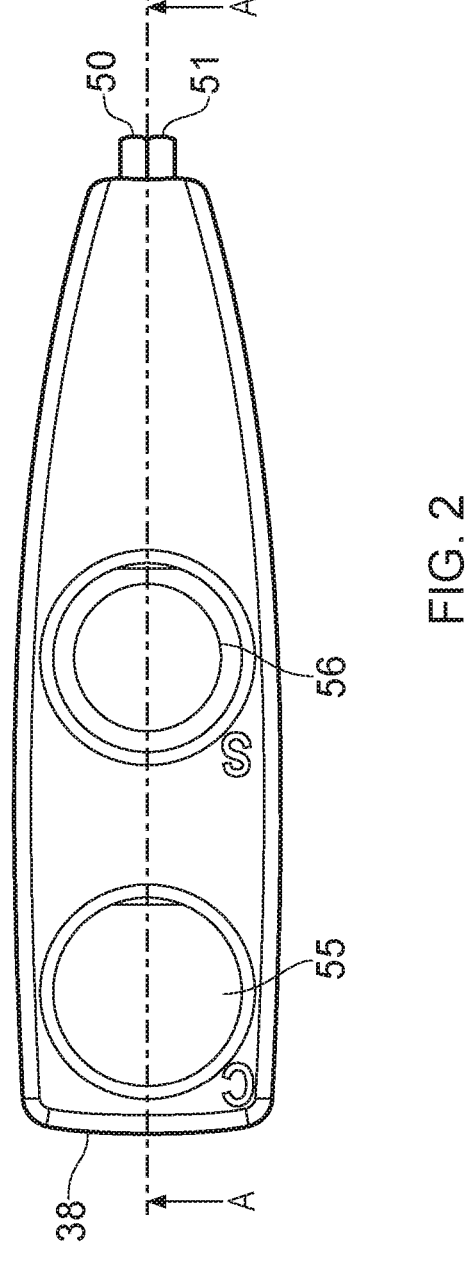
FIG. 2 shows the bottom profile of the device. A first projection (55) controls the flow of contrast, and a second projection controls the flow of saline (56). Tubing outlet ports for contrast (50) and saline (51) are formed in the housing (38).
Figure 3:
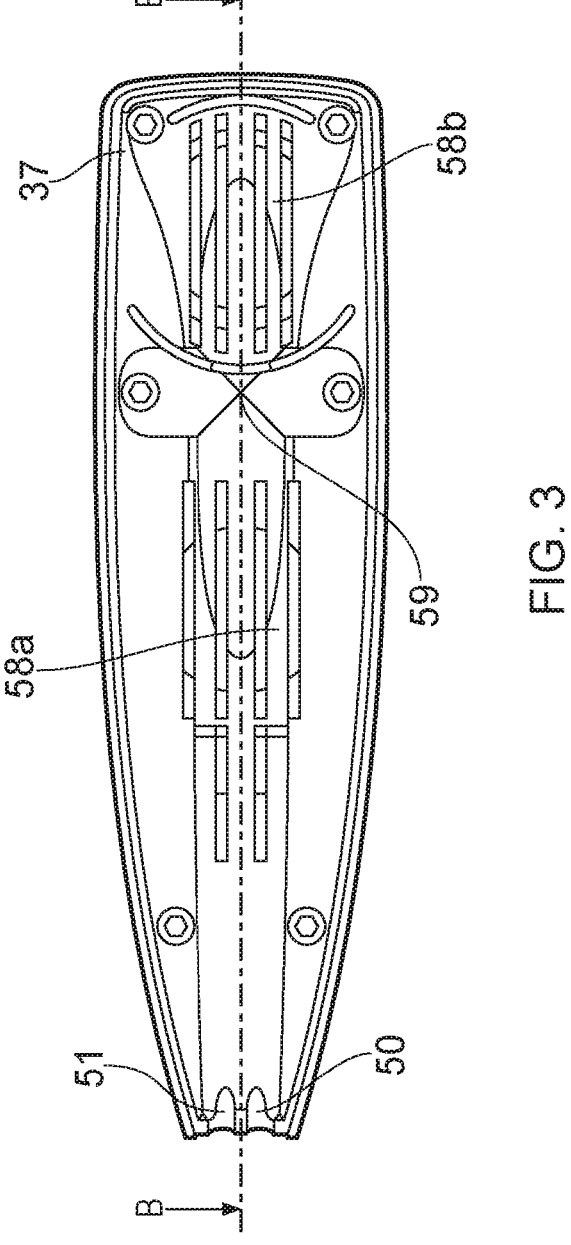
FIG. 3 shows the top profile view of the device. The top housing (37) has circular finger holds (58a, 58b) and a cruciform design (59). Tubing outlet ports for contrast (50) and saline (51) are formed in the housing (37).
Figure 4:
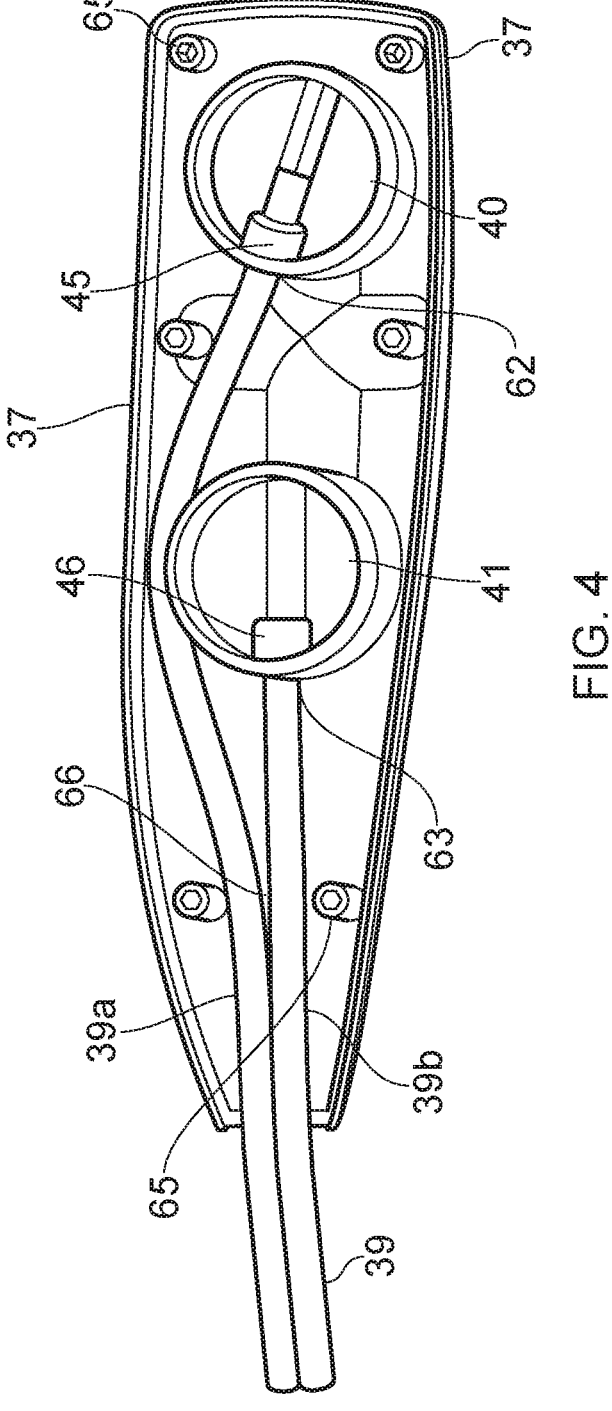
FIG. 4 shows the internal view of the device, chambers and tubing connections. Twin tubing (39) is bifurcated at a point (66) inside the housing (37). One fluid conduit line (39a) is in fluid flow communication with a first chamber (40) and a second fluid conduit line (39b) is in fluid flow communication with a second chamber (41). Each chamber base has an outlet (45, 46) with an adjacent connection point (62, 63) where a fluid conduit line (39a, 39b) is inserted and bonded to the connection point (62, 63). Six female spigot points (65) are positioned on the inner face of the top housing (37).
Figure 5:
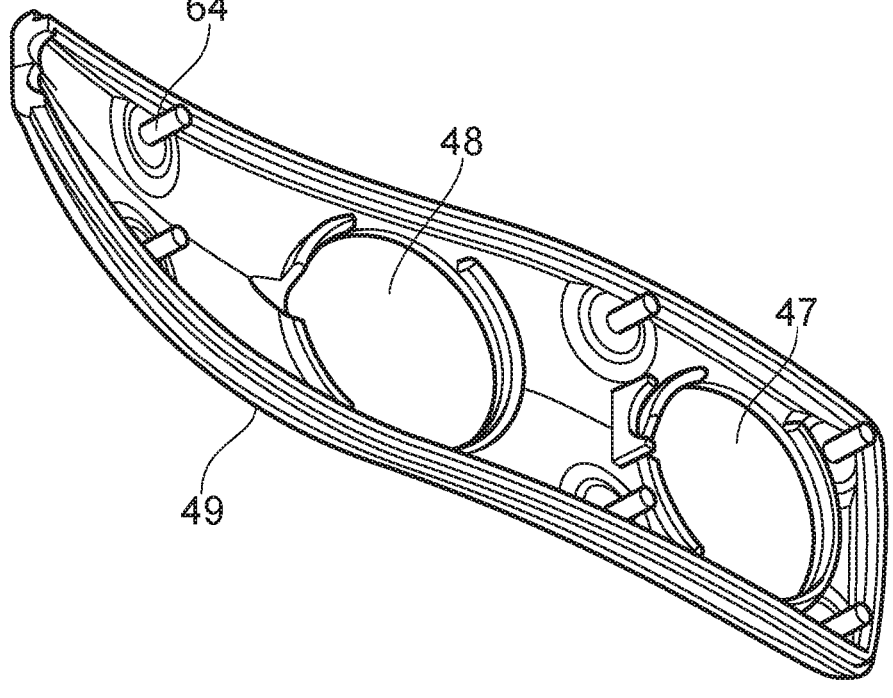
FIG. 5 shows a view of the inner face of the bottom housing (38). Two apertures (47, 48) are formed in the bottom housing (38). Six male spigots (64) are formed in the surface of the inner face of the bottom housing (38).
Figure 6:
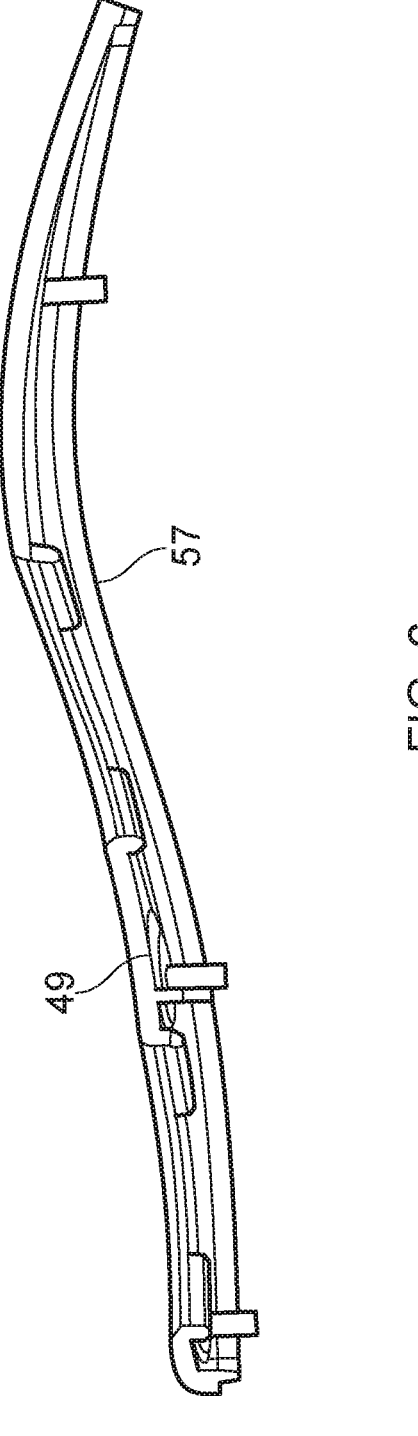
FIG. 6 shows the side view of the bottom housing.
Figure 7:
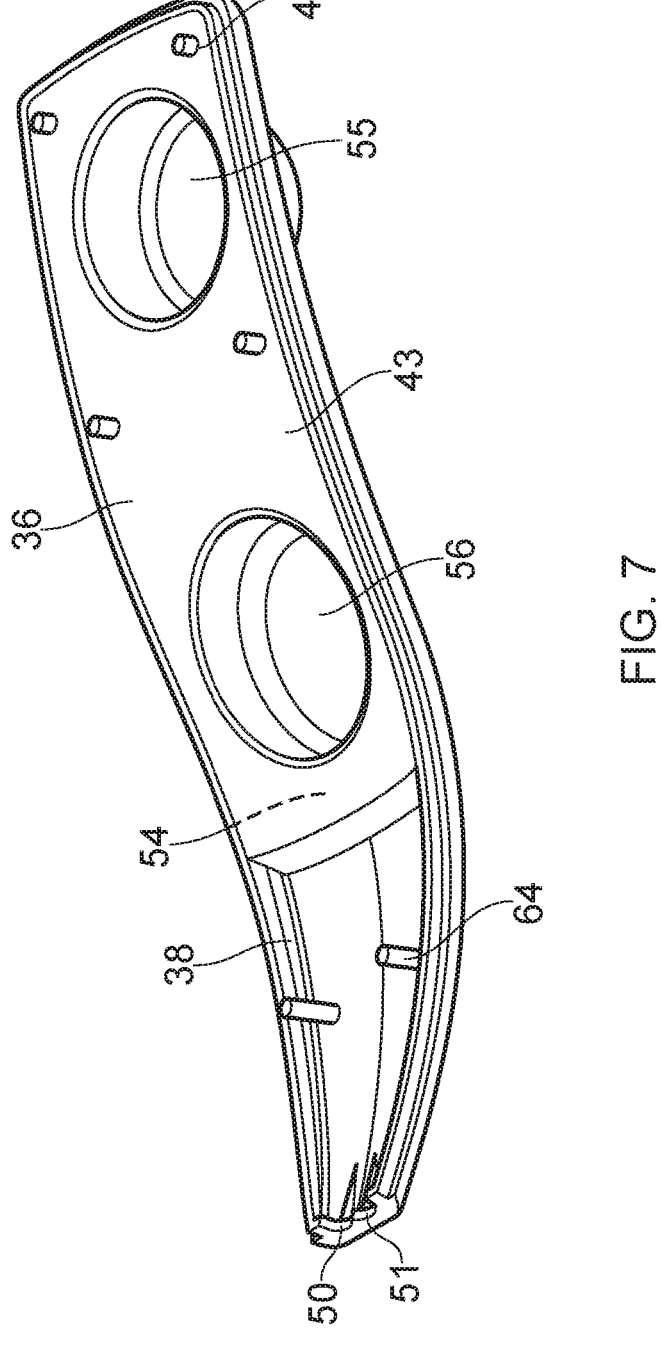
FIG. 7 shows the interior view of the device and the assembly of the pressure control sheet (36) to the bottom housing (38). The spigots (64) of the bottom housing (38) are inserted through the holes of the pressure control sheet (36).
Figure 8:
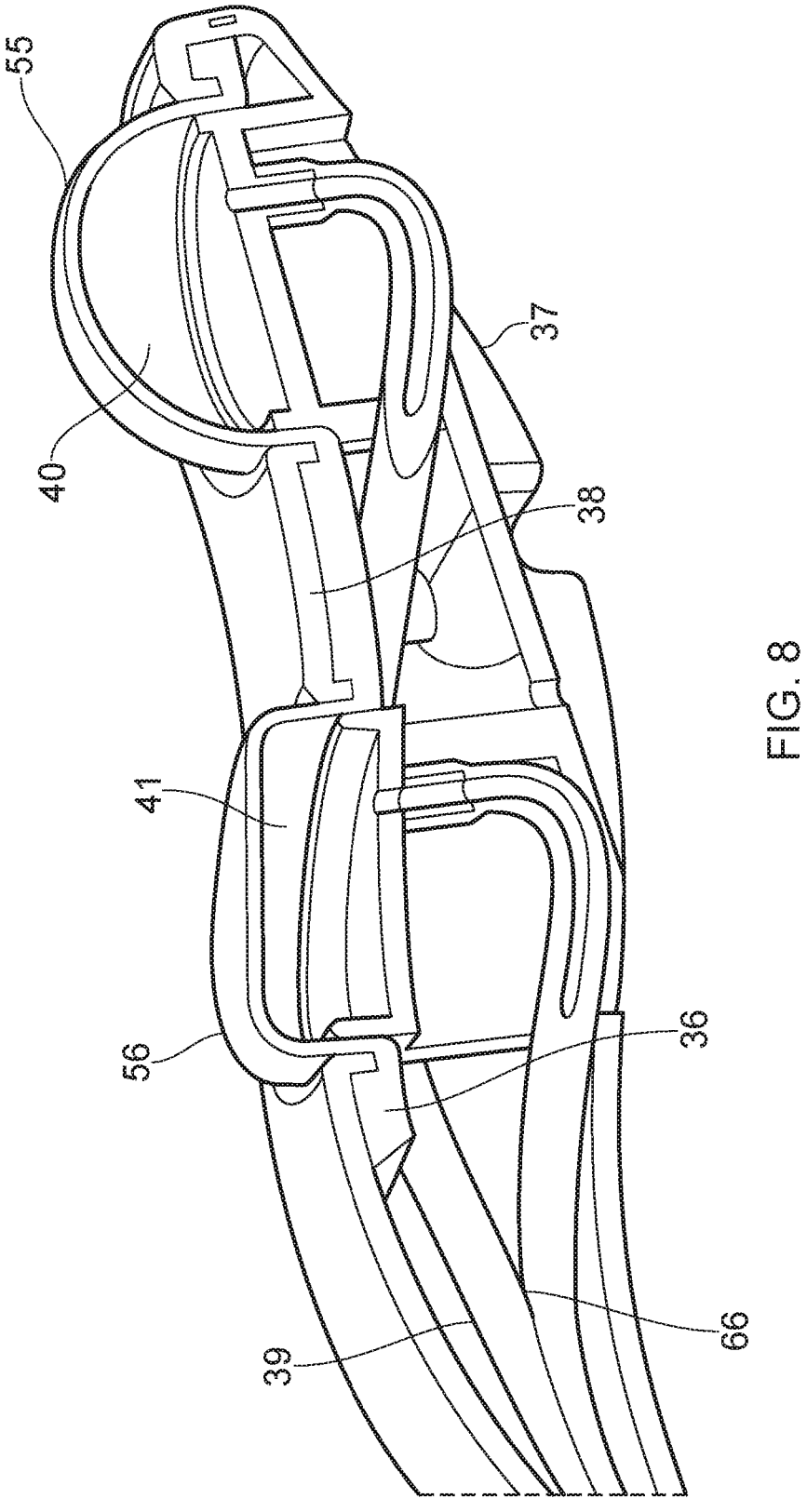
FIG. 8 is a section through the device showing the chambers (40, 41) formed by the bottom housing (38), pressure control sheet (36) and top housing (37). Two projections (55, 56) extend through two apertures in the bottom housing (38). Twin tubing (39) is bifurcated at a point (66) inside the housing. Each fluid conduit line is in fluid-flow communication with a chamber (40, 41).

The control device, as shown in FIGS. 1-8, will rest on the patient's drape where the cardiologist or clinical operator will use it to regulate the flow of fluids into the coronary arteries. This area is known as the "sterile field."

The housing (37, 38) is plastic and distinctively coloured to easily identify it on what may be a busy sterile field. On the housing are two buttons (55, 56) for the control of contrast, the upper domed button (55) and saline, the lower flat button (56). These are indicated on the housing as "C" and "S".

Twin tubing (39) connects the housing to the machine with standard, industry practice, Luer Lock connectors (52, 53) at the end of each of fluid conduit line (39a, 39b). The Luer Lock connectors are different on each conduit line so that connection is clear for each different fluid and sensor.

The tubing length allows connection to the ACIST CVi® machine and permits easy manipulation and management by the cardiologist or clinical operator.

The shape of the control device is designed to fit comfortably in the operator's hand and to naturally handle the manipulation of the buttons (55, 56) with first and second fingers. Some operators will use other finger combinations to suit their personal preference and maintain adequate control. The shape includes an obtuse angle (57) to facilitate hand holding and a ribbed surface for handling with hands which may either be gloved and/or wet. Each of the buttons (55, 56) may be compressed to activate the flow of a column of air to the sensor of choice. The colour of the plastic used for the top and bottom housings (37, 38) is distinctive so as to clearly identify the component on what may be a busy "sterile field." Purple stands out clearly against the blue or green colour of the drape. Purple is also the colour of the currently used device.

The control device has six elements and one item of packaging:

1. Top housing (37)
2. Bottom housing (38)
3. Pressure control sheet (36)
4. Twin tubing (39)
5. Male Luer Lock connector (52)
6. Female Luer Lock connector (53)
7. Packaging Top Housing The outer face of the top housing (37) includes two circular, ribbed finger holds (58a, 58b), which enable the element to be handled with gloved and/or wet hands. There is also a cruciform design (59) positioned between the two circular ribbed finger holds (58a, 58b), which serves in the same way for safe handling and manipulation.

The inner face of the top housing (37) is designed to support the pressure control sheet (36) and provides the base of the two airflow chambers (40, 41). Each airflow chamber base has an outlet (45, 46) with an adjacent connection point (62, 63) where a fluid conduit line (39a, 39b) is inserted and bonded to the connection point (62, 63) to form a leak-proof and airtight connection.

The top housing (37) and the pressure control sheet (36) form two airflow chambers (40, 41) having a prescribed volume of air that is fundamental to the function of the device. When finger pressure is applied to one of the buttons (55, 56), a column of air is pushed through an outlet (45, 46) of the airflow chamber (40, 41) and carried through the fluid conduit line (39a, 39b), through the Luer Lock connector (52, 53) and to the sensor of the machine.

Six female spigot points (65) are positioned on the inner face of the top housing (37) around the sides of the top housing (37) to enable it to be securely joined to the bottom housing (38) through the pressure control sheet (36).

The top housing is designed from a speciality plastic which is both rigid and flexible. This means that the material is strong enough to support the pressure control sheet but soft enough to enable easy handling and manipulation. There are soft edges to the design to prevent cutting or damage to other components in the pack or damage to users.

Bottom Housing

The bottom housing (38) is designed to support the pressure control sheet (36) and to mate perfectly with the top housing (37), through the six holes (44) in the pressure control sheet (36), to form the two airtight, leak-proof airflow chambers (40, 41) which form the key functional elements of the device.

The bottom housing (38) has two large 1.2 cm wide circular apertures (47, 48). These apertures (47, 48) match with the button projections (55, 56) of the pressure control sheet (36). The two raised button projections (55, 56) of the pressure control sheet (36) protrude through the apertures (47, 48) and form compressible, supported, operable buttons (55, 56) when assembled. Pressing the buttons (55, 56) creates positive air pressure and activates the flow of air columns to the sensors.

Six male spigots (64) are positioned on the inner face of the bottom housing (38) around the sides of the bottom housing (38) to enable it to be securely joined to the top housing (37) through the holes (44) of the pressure control sheet (36). The male spigots (64) mate with the female spigot points (65) and are joined with pressure in a manufacturing jig to form a safe, secure crimped seal between the top housing (37) and the bottom housing (38), with the pressure control sheet (36) held securely between. The orientation of the assembled device is top housing (37), pressure control sheet (36), bottom housing (38).

The bottom housing (38) is designed from the same speciality plastic as the top housing (37). The mouldings of each element of the housing (37, 38) have been designed to have smooth profiles which result in soft edges without sharpness to avoid potential cutting edges which may damage other pack components or injure the operator.

Pressure Control Sheet

The pressure control sheet (36) is designed to fit between the top housing (37) and the bottom housing (38). It incorporates two raised profile buttons (55, 56) which are designed to be compressed as the trigger for creation of positive air pressure within the airflow chambers (40, 41). The air column then will flow through the selected twin tubing conduit lines (39a, 39b) and activate the sensors within the ACIST CVi® machine. The upper button (55) is a domed, hemispheric design for use with contrast while the lower button (56) has a raised but flat profile, hemi-cylindrical in shape, for use with saline.

Six holes (44) extend through the pressure control sheet (36) and are located around the sides of the pressure control sheet (36). These holes (44) enable the pressure control sheet (36) to be securely held by the mating male spigots (64) and female spigot points (65) of the bottom housing (38) and top housing (37), respectively.

The pressure control sheet (36) is designed from a speciality plastic which is soft for finger compression, supple, resilient and flexible. This means that the specific material is strong enough to allow repeated compression with finger pressure but soft enough to ensure ease of compression and rapid recovery of its uncompressed shape.

The material from which the pressure control sheet (36) is made has been tested to allow multiple compressions within the operating time of an angiography and/or PCI. The material will be compressed and after each compression will resume its original shape and form. The material has a specific Shore hardness and chemical compound to operate optimally within the required specifications of the procedures for which it will be used.

The material from which the pressure control sheet (36) is made has a very specific chemical compound which does not include phthalates and therefore has a lower risk of causing a carcinogenic reaction. This translates into a safer patient and user outcome and is in line with new emerging regulatory requirements within the medical device industry.

Twin Tubing

The twin tubing (39) has two fluid conduit lines (39a, 39b) for air flows. It enables the transfer of the exact volume of air from the airflow chambers (40, 41) to the machine sensors, without the loss of any volume. The volume is created when the buttons (55, 56) are compressed and this creates positive air pressure which transmits signals as columns of air through the twin tubing (39) to the sensors in the machine.

The twin tubing (39) is approximately 180 cms in length to link the control device to the machine over the sterile field. The length makes it possible for the cardiologist or clinical operator to manipulate the tubing by hand without restriction. The length also maintains a safe distance from the patient's sterile field to the non-sterile area where the machine is positioned. This is a part of the hospital's protocol for the maintenance of hygiene within the medical operating environment.

The design of the twin tubing (39) is standard with an internal diameter of 1.6 mm and an external diameter of 3.2 mm. This tubing is called "monitoring tubing" within the medical device industry. The twin tubing (39) is transparent to allow the detection of air bubbles when it is used with fluids. A tint of colour may be used in the saline conduit line (39*b*) to differentiate it from the contrast conduit line (39*a*). This is a safety feature to assist in the correct set up of the system to avoid accidental misconnection by clinical users.

The twin tubing (39) is bifurcated inside the top housing (37) to enable the connection of the contrast conduit line (39*a*) to one airflow chamber (40) and the saline conduit line (39*b*) to the second airflow chamber (41). The twin tubing (39) is also bifurcated at the end connected to the Luer Lock connectors, to enable the separate connections of the contrast conduit line (39*a*) and the saline conduit line (39*b*).

The twin tubing (39) is designed from a standard plastic material such as PVC comprising DEHT which is both rigid to support the flow of fluids or air and flexible enough to permit easy handling and manipulation by hand.

Luer Lock Connector, Male, for Contrast

The male Luer Lock connector (52) is an industry standard element which is routinely used to connect tubing of different sizes or hardnesses or to connect tubing to fixed points on machines or other equipment. In this case the male Luer Lock connector (52) enables a smooth flow of air or fluid between the contrast fluid conduit line (39*a*) and the sensor input on the machine. The male Luer Lock connector (52) forms a leak proof and airtight joint between the contrast fluid conduit line (39*a*) and equipment.

The design is rigid to permit safe, secure, tight connection, yet flexible enough to permit easy handling and manipulation. A male Luer Lock connector (52) defines this conjunction of the contrast conduit line (39*a*) and machine. The male Luer Lock connector (52) conjoins with the female Luer Lock on the sensor. The male Luer Lock connector (52) ensures that there is no accidental misconnection of contrast to the saline sensor, for example, or vice versa.

The male Luer Lock connector (52) is designed from rigid plastic material, for example PVC or Polycarbonate, which will allow easy connection and hand-held manipulation for connecting and disconnecting the fluid conduit lines (39*a*, 39*b*) from the machine.

Luer Lock Connector, Female, for Saline

The female Luer Lock connector (53) is an industry standard element which is routinely used to connect tubing of different sizes or hardnesses or to connect tubing to fixed points on machines or other equipment. In this case the female Luer Lock connector (53) enables a smooth flow of air or fluid between the saline fluid conduit line (39*b*) and the sensor input on the machine. The female Luer Lock connector (53) forms a leak proof and airtight joint between the saline fluid conduit line (39*b*) and equipment.

The design is rigid to permit safe, secure, tight connection, yet flexible enough to permit easy handling and manipulation. A female Luer Lock connector (53) defines this conjunction of the saline conduit line (39*b*) and machine. The female Luer Lock connector (53) conjoins with the male Luer Lock on the sensor. The female Luer Lock connector (53) ensures that there is no accidental misconnection of saline to the contrast sensor, for example, or vice versa.

The female Luer Lock connector (53) is designed from rigid plastic material, for example PVC or Polycarbonate, which will allow easy connection and hand-held manipulation for connecting and disconnecting the fluid conduit lines (39*a*, 39*b*) from the machine.

Packaging

The paper peel pouch is designed to protect devices against tampering or unintentional damage prior to placement within a procedure pack.

Packaging ensures that the regulatory control of the CE Mark is protected as long as possible while the device is in the process of being processed and manufactured as a component into the finished procedure pack. This is a standard convention for selected higher value or technical items within the medical device industry.

The packaging is manufactured from a standard combination of paper and cellophane as a pouch which will permit Ethylene Oxide gas sterilisation of the packaged device and the safe storage of the product subsequently. The package will be sealed prior to shipment so that the device is protected in its non-sterile state. It may or may not be left inside this packaging by the kit packer when putting it into a procedure pack. However, the presence of packaging with the manufacturer's CE Mark attached protects the liability of the manufacturer from legal action in certain situations.

Assembly of the Device

The twin tubing (39) is bifurcated to facilitate easy handling and management. It enables a first fluid conduit line (39*a*) of the twin tubing (39) to be separated from a second fluid conduit line (39*b*) of the twin tubing (39). The first fluid conduit line (39*a*) is connected by chemical bonding to one of the airflow chambers (40). The second fluid conduit line (39*b*) is then connected by chemical bonding to the second airflow chamber (41). The twin tubing (39) is separated just above the outlet from the conjunction of the top and bottom housing (37, 38). This is at, or above the point; where the twin tubing (39) emerges from the housing assembly (37, 38). This holds the integrity of the twin tubing (39) over its workable length but separates one conduit line (39*a*) from the other (39*b*) at a bifurcation point (66) for connection to each airflow chamber (40, 41) within the housing (37, 38).

The top housing (37), with the first and second fluid conduit lines (39*a*, 39*b*) attached, is then connected via the spigot system (64, 65) to the bottom housing (38) with the pressure control sheet (36) in place, positioned inside the bottom housing (38). The pressure control sheet (36) is placed so that each button (55, 56) correspondingly fits into the relevant apertures (47, 48) in the bottom housing (38). Once the pressure control sheet (36) is firmly positioned within the bottom housing (38) with the male and female spigots (64, 65) lined up through the holes (44) in the pressure control sheet (36), then the device is ready for closing. A manufacturing assembly jig will be used to secure the crimping of the three components (36, 37, 38) together securely.

The Luer Lock connectors (52, 53) are chemically bonded to the twin tubing fluid conduit lines (39a, 39b). After a few seconds, the chemical bond will be secure, connecting the fluid conduit lines (39a, 39b) to the Luer Lock connectors (52, 53). The male Luer Lock connector (52) is chemically bonded to the contrast fluid conduit line (39a) and the female Luer Lock (53) is chemically bonded to the saline fluid conduit line (39b). The twin tubing (39) is separated by hand for a consistent distance from the Luer Lock connectors (52, 53), for example, 4 or 5 cm from the Luer Locks connectors (52, 53).

The device may need to be loosely coiled for placement into the packaging. The packaging is sealed and labelled, ready for shipment to the kit packer. An Instruction for Use (IFU) will be added to each carton of packaged devices to assist the user in the set up procedure. This will be in accordance with local regulations.

Function of the Device

Compression of the contrast button (55) is made fully to calibrate the system. The selection of the required volume for each infusion is then entered on the LED screen on the ACIST CVi® pump. Calibration has now been completed. Normally for left heart studies a volume of 10 ml is used for each infusion. For right heart studies 3 or 4 ml infusions are commonly preferred. No calibration is required for the saline function as this is not volume critical at any stage during angiography or PCI. The volume of contrast infused is kept to a minimum to reduce the risk of nephrotoxicity, which is a well recorded side effect of over infusion of contrast media.

During a typical angiography and/or PCI the volume of contrast infused will normally be 60 ml for an angiography and 150 ml for a PCI. Therefore, the maximum number of compressions made, including the initial calibration compression, will be 7-16. Saline will usually involve a maximum of five compressions initially during the priming stage of the set up procedure when air is being removed from the circuit of tubing and manifold kit. The volume of contrast to be infused is always carefully monitored as there is evidence of nephrotoxicity associated with the over infusion of contrast.

After calibration, the contrast button (55) will be compressed to set up a chain of actions which will send a fraction of contrast into the selected coronary artery. The contrast button (55) is compressed and released, the volume of contrast being infused shows on the LED screen on the ACIST CVi® injector. The compression of the contrast button (55) creates a positive air pressure which transmits a column of air down the contrast fluid conduit line (39a) of the system. When the air column hits the sensor it activates the sensor which in turn activates the pump and the appropriate volume of fluid is released into the selected coronary artery. The cardiologist or clinical operator looks at the screen above the patient and sees the image made by the contrast in the artery and he/she can detect the area of concern for further investigation, diagnosis, or for PCI as a follow on procedure, with the placement of a stent or deployment of a balloon catheter.

Within the system there is also a contrast injector syringe. The initial diagnostic infusions are sometimes called "scouting" injections. They show the vessels and coronary arteries in profile, always in 2D and sometimes in 3D, depending on the equipment being used within the hospital. However, the pressure of each injection is not high enough to get contrast and therefore visualisation within the heart structure itself i.e. beyond the heart valves into the heart chambers. Using a High Pressure contrast injector syringe will enable as much as 25 ml to be injected in 0.5 seconds and this will then show the detailed structure up well on the fluoroscope screen.

To enable this to be done, each hand controller kit from ACIST® also includes a High Pressure line and High Pressure stopcock. Typical pressures used are up to 650 psi but the tubing is rated at 1200 psi although such high pressures are very rarely used as they would damage the heart. The decision to employ the high pressure option is again selected on the LED screen on the ACIST CVi® injector. The stopcock provides an on/off function within the HP line circuit.

Design and Materials

The design of the control device also has operating advantages over the currently used product. It has a newer, safer, modern design and modern materials with safety advantages.

The control device uses a flat pressure control sheet (36) moulding profile which maintains an even and simpler manufacturing solution than that of the prior art. The prior art functions with bladders which are moulded from plastic in which it is difficult to form a consistent surface for compression. There have been reported incidents with pin holes developing in the plastic material of the prior art. The presence of pin holes has been reported to cause the device not to function adequately as the airflow chambers are not leak-proof. With the present invention, there is a reduced risk of leaks caused by pinholes because the moulding and design are easier to manufacture, therefore reducing the risk of non-functioning.

The airflow chambers (40, 41) in the top housing (37) are rigid structures which form the base of each functional chamber (40, 41) in conjunction with the leak-proof seal made with the pressure control sheet (36). The airflow chambers (40, 41) are less open to possible movement compared with the two-part bladder construction of the prior art. Similarly the pressure control sheet (36) incorporates two separate buttons (55, 56) for contrast and saline in a single element. This design avoids the risk of non-recovery of each bladder after button compression. This problem with the devices of the prior art has been reported by a number of clinical users. When a hand controller does not resume its shape after compression it is usually discarded in favour of a new one, with the associated cost and inconvenience. The current device also has a series of complex channels inside the top housing to hold the bifurcated twin tubing. This has been improved to reduce manufacturing assembly time and costs within the design of the control device.

The twin tubing (39) and pressure control sheet (36) are made with DEHP-free chemical components which reduce the risk of carcinogenic reactions. Currently used devices do not have these advantages.

The securing of the pressure control sheet (36) within the sandwich created by the top and bottom housing (37, 38) is achieved by the placement of six spigots (64, 65) around the edge of the mouldings to create a robust and secure structure. This design results in there being less chance of the pressure control sheet (36) becoming misaligned with the base of each airflow chamber (40, 41) and this ensures the effective, repeated functioning of the control device.

On the outer face of the top housing (37) there are two ribbed finger holds (58a, 58b) which facilitate the safe management and manipulation of the device when hands are either gloved or wet during an angiography and/or PCI procedure. This improvement has been made to reduce the cycle time for moulding and this, in turn, reduces the volume of material used during the moulding process. This reduction in material will also reduce the cost of each component in manufacture. These finger holds (58*a*, 58*b*) are regarded as being a distinctive feature against the currently used device.

Modern, safer materials have been used to reduce cost and to reflect the market needs. These materials are free of phthalates which are potentially carcinogenic. DEHT plastic is phthalate-free and has been used in the manufacture of the control device. The pressure control sheet (36) and twin tubing (39) are constructed from this specific material formulation. None of the other components within the control device design contain phthalates. The currently used device does not have this advantage.

The control device is constructed from six separate components. The design of the housing (37, 38) conveys a safer and more cost effective construction which represents improvements over the currently used device. These improvements reduce the risk of malfunction and associated increase in operational costs. Finger holds (58*a*, 58*b*) differentiate the appearance against the currently used device and enable safe holding with gloved and/or wet hands. Newer, modern materials convey safety advantages over the currently used brand. The convenience and reduction in set up time associated with the control device's design for inclusion in packs is paramount as this is what customers have long been requesting. The control device represents a significant advance over current technology and will provide a new standard of performance for hand controllers used with the ACIST CVi® injector.

The invention claimed is:

1. A control device for providing a fluidic signal to a medical infusion apparatus, the device comprising:
   (a) a housing (37, 38), wherein the housing defines a wall (49) enclosing a housing interior;
   (b) a pressure control sheet (36) comprising at least two projections (55, 56),
   wherein the pressure control sheet is formed from a deformable and resilient material,
   wherein at least a portion of the pressure control sheet (36) is positioned within the housing interior,
   and wherein the pressure control sheet is secured to and forms a seal with the housing such that the housing and the at least two projections together define a first chamber (40) and a second chamber (41),
   wherein the second chamber is independent of the first chamber,
   wherein the pressure control sheet is arranged so that fluid pressure within each chamber can be changed upon input from a user; and (c) a first fluid conduit member (39*a*) in fluid-flow communication with the first chamber and a second fluid conduit member (39*b*) in fluid-flow communication with the second chamber,
wherein, in use, a first input from a user changes the fluid pressure within the first chamber which causes movement of fluid through the first fluid conduit member to provide a first fluidic signal, and a second input from a user changes the fluid pressure within the second chamber which causes movement of fluid through the second fluid conduit member to provide a second fluidic signal.

2. A control device according to claim 1, wherein the pressure control sheet (36) is formed from a unitary piece of material.

3. A control device according to claim 1, wherein the pressure control sheet (36) is contacted on an upper surface and a lower surface by the housing (37, 38) to create a seal.

4. A control device according to claim 1, wherein the at least two projections are formed in a same surface of the pressure control sheet.

5. A control device according to claim 1, wherein the at least two projections (55, 56) are substantially hemispherical and/or cylindrical.

6. A control device according to claim 1, wherein the housing (37, 38) is in contact with an upper surface (54) of the pressure control sheet and a lower surface (43) of the pressure control sheet to secure the pressure control sheet (36) to the housing (37, 38).

7. A control device according to claim 6, wherein the pressure control sheet (36) has a plurality of holes (44) and the pressure control sheet is secured through the plurality of holes.

8. A control device according to claim 1, wherein the pressure control sheet (36) is formed from a plastic, preferably a phthalate-free plastic such as PVC comprising DEHT.

9. A control device according to claim 1, wherein the wall (49) defines at least two apertures (47, 48), and wherein at least a portion of the pressure control sheet (36) extends through the at least two apertures (47, 48).

10. A control device according to claim 1, wherein each chamber (40. 41) has a volume selectively adjustable to change the fluid pressure within said chamber.

11. A control device according to claim 1, wherein the housing (37, 38) is textured.

12. A control device according to claim 1, wherein the fluid conduit members (39*a*, 39*b*) are connected to the chambers (40, 41) via apertures (50, 51) in the housing (37, 38).

* * * * *